United States Patent [19]

Fowler

[11] Patent Number: 5,964,698
[45] Date of Patent: Oct. 12, 1999

[54] SLIDING HOOK ASSEMBLY FOR USE WITH A SURGICAL RETRACTOR STAY APPARATUS AND METHODS FOR USE

[75] Inventor: James M. Fowler, Houston, Tex.

[73] Assignee: Lone Star Medical Products, Inc., Houston, Tex.

[21] Appl. No.: 09/234,560

[22] Filed: Jan. 20, 1999

[51] Int. Cl.⁶ .................................................. A61B 17/00
[52] U.S. Cl. .......................... 600/217; 600/231; 600/201; 24/130
[58] Field of Search .................................... 600/201, 210, 600/213, 214, 217, 226, 227, 231, 233; 24/130

[56] References Cited

U.S. PATENT DOCUMENTS

| | | | |
|---|---|---|---|
| Re. 32,021 | 11/1985 | Scott, Jr. .............................. | 600/233 X |
| 170,573 | 11/1875 | Lesh ...................................... | 24/300 X |
| 334,711 | 1/1886 | Lorenz ............................ | 24/265 EE X |
| 3,515,129 | 6/1970 | Truhan . | |
| 3,542,015 | 11/1970 | Steinman ............................ | 600/206 X |
| 3,655,964 | 4/1972 | Slight ................................. | 250/43.5 D |
| 3,749,088 | 7/1973 | Kohlmann . | |
| 3,762,401 | 10/1973 | Tupper . | |
| 3,916,879 | 11/1975 | Cotten . | |
| 4,048,987 | 9/1977 | Hurson ................................... | 600/206 |
| 4,178,661 | 12/1979 | Klein ........................................ | 24/130 |
| 4,185,636 | 1/1980 | Gabbay et al. ...................... | 128/334 R |
| 4,190,042 | 2/1980 | Sinnreich . | |
| 4,254,763 | 3/1981 | McCready et al. . | |
| 4,257,406 | 3/1981 | Schenk . | |
| 4,263,900 | 4/1981 | Nicholson . | |
| 4,274,398 | 6/1981 | Scott, Jr. . | |
| 4,321,916 | 3/1982 | McKee . | |
| 4,337,762 | 7/1982 | Gauthier . | |
| 4,337,763 | 7/1982 | Petrassevich . | |
| 4,344,420 | 8/1982 | Forder . | |
| 4,355,631 | 10/1982 | LeVahn . | |
| 4,380,999 | 4/1983 | Healy . | |
| 4,387,706 | 6/1983 | Glass . | |
| 4,412,532 | 11/1983 | Anthony . | |
| 4,421,107 | 12/1983 | Estes et al. . | |
| 4,421,108 | 12/1983 | Cabrera et al. . | |
| 4,430,991 | 2/1984 | Darnell ................................. | 600/233 X |
| 4,434,791 | 3/1984 | Darnell .................................... | 600/233 |
| 4,559,677 | 12/1985 | Tracy ......................................... | 24/300 |
| 4,685,467 | 8/1987 | Cartmell et al. ........................ | 128/640 |
| 5,080,088 | 1/1992 | LeVahn ................................... | 600/206 |
| 5,141,973 | 8/1992 | Kobayaski et al. ..................... | 523/300 |
| 5,231,974 | 8/1993 | Giglio et al. ............................. | 600/206 |
| 5,260,576 | 11/1993 | Sommer, Jr. et al. ............... | 250/359.1 |
| 5,307,805 | 5/1994 | Byrne ................................. | 600/227 X |
| 5,518,124 | 5/1996 | Sommer, Jr. et al. .................. | 209/577 |
| 5,738,224 | 4/1998 | Sommer, Jr. et al. .................. | 209/588 |
| 5,769,783 | 6/1998 | Fowler ................................... | 600/226 |
| 5,785,649 | 7/1998 | Fowler, Jr. .............................. | 600/233 |

FOREIGN PATENT DOCUMENTS

| | | |
|---|---|---|
| 1222141 | 2/1971 | United Kingdom . |
| 1550254 | 8/1979 | United Kingdom . |
| 1550255 | 8/1979 | United Kingdom . |

OTHER PUBLICATIONS

Bone Retractors and Retractors AESCULAP®, Product catalog, 2 pages (no date).

*Thermoplastic Replaces Metal In Disposable Abdominal Retractor*, MD&M Review, ULTOP® Conveyor Modules (no date).

I.S.I. North America, Inc. *International Surgical Instruments*, Brochure (no date).

Accurate Surgical & Scientific Instruments Corporation Brochure, p. 39 (no date).

*Primary Examiner*—Jeffrey A. Smith
*Attorney, Agent, or Firm*—Akin, Gump, Strauss, Hauer & Feld, L.L.P.

[57] ABSTRACT

The sliding hook assembly has an integrally formed handle body encapsulating a hook member which can be used to engage a physical restraint in the surgical field in the absence of the use of a slotted surgical retractor frame. The sliding hook assembly further includes an opening with a notch for receiving and securing the elastic member of a surgical retractor stay.

53 Claims, 2 Drawing Sheets

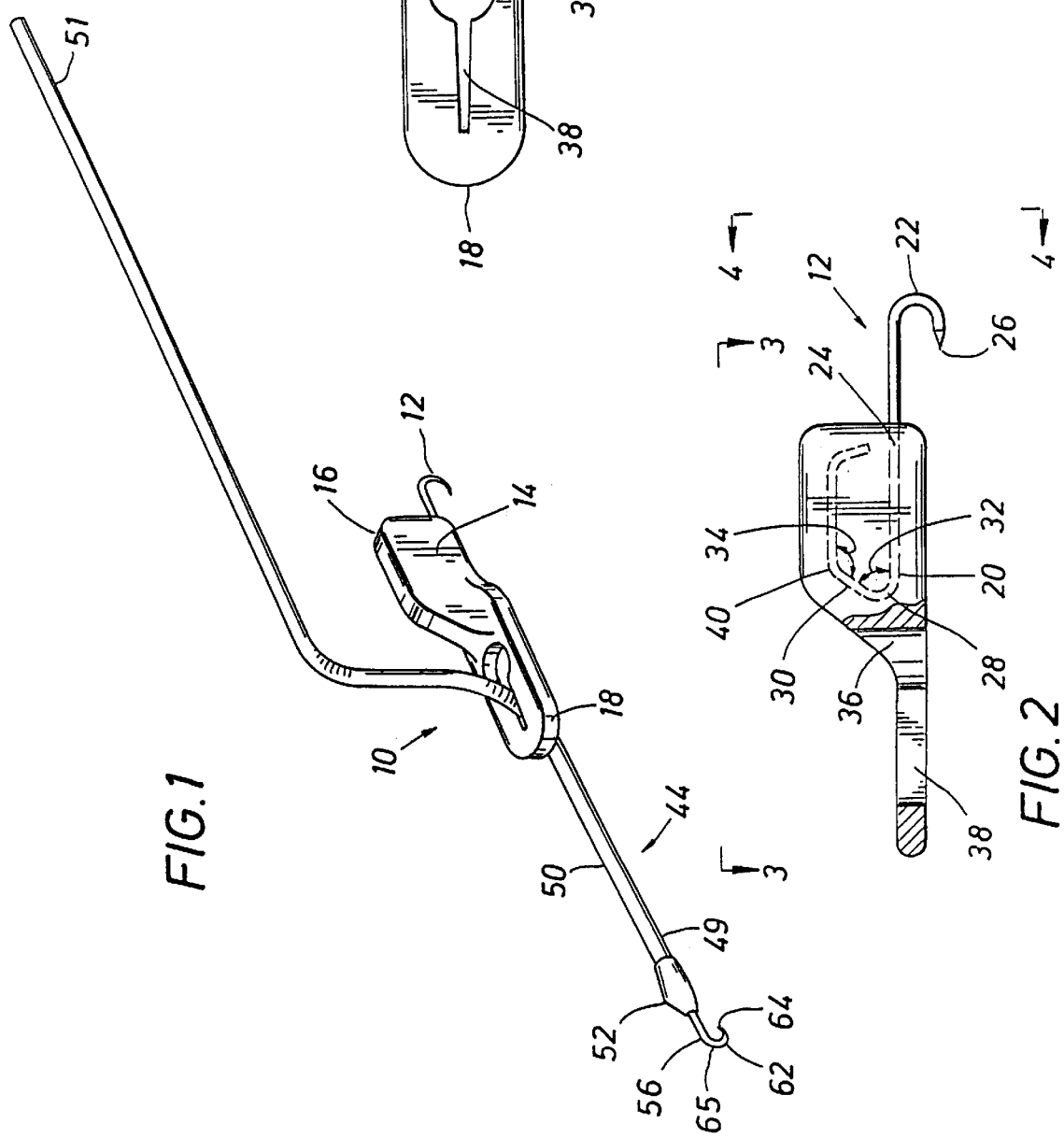

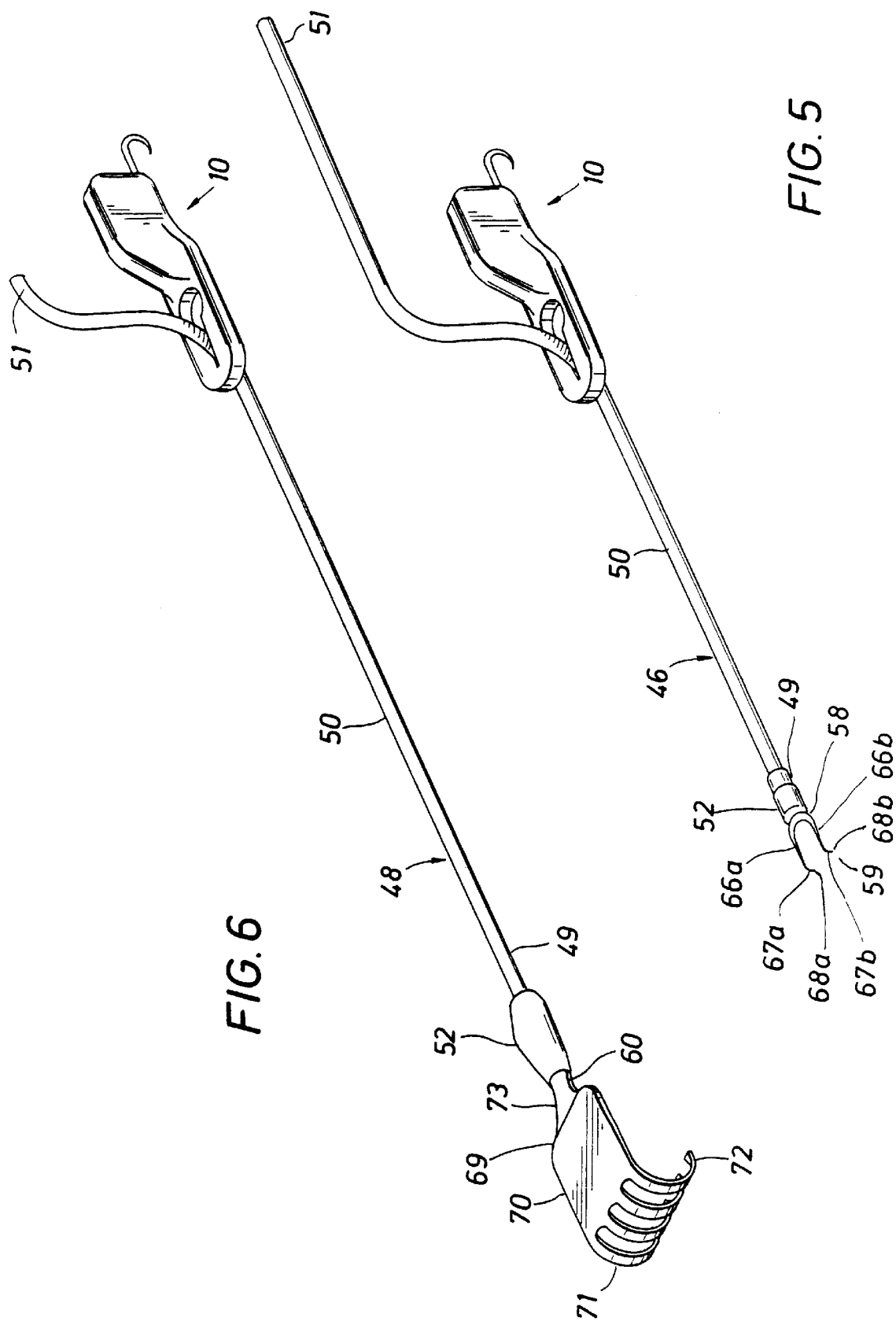

SLIDING HOOK ASSEMBLY FOR USE WITH A SURGICAL RETRACTOR STAY APPARATUS AND METHODS FOR USE

SPECIFICATION

BACKGROUND OF THE INVENTION

1. Field of the Invention

The present invention relates to surgical retractors and surgical retractor stays. More particularly, the present invention relates to a sliding hook assembly for receiving and securing a surgical retractor stay wherein the sliding stay hook engages a surgical drape or other physical restraint in or near the surgical field.

2. Description of the Related Art

During the course of a surgical procedure or operation, the surgeon opens the patient with a scalpel, forming an incision and surgical site. As the surgeon cuts deeper, the operating room staff typically holds tissue away from the operative field using retractors.

Most retractors are one piece metallic implements that retract a wound in a non-yielding manner. Manipulation and movement of the surgeon as well as movement caused by the contracting muscles or tissues of the patient can result in bruising or tearing of the tissue.

Once an incision is separated and retracted, there is often a need for multiple stays in the form of sutures for holding various tissues, for example different organs. Elastic surgical retractor stay systems are in commercial use that include elastic stays, each having an elongated elastic member that is typically a hollow length of elastic tubing. The elastic tubing provides proximal and distal end portions. The distal end portion carries an elongated hook constructed of wire.

The wire hook has a proximal end that is placed in the distal end of the bore of the hollow tubing. A shrink wrap is placed over the hook and tubing to hold the proximal end of the wire hook firmly in position within the bore of the tubing at the distal end. The embedded portion of the wire hook member is usually recurved or folded. This folded proximal portion of the wire hook expands in the tubing slightly, forming a vertically extended portion that defines a handle.

Various patents have issued for elastic stay retractor systems. A surgical retractor stay and surgical retractor stay system is disclosed in U.S. Pat. No. 5,785,649 to James M. Fowler, Jr. on Jul. 28, 1998. The surgical retractor stay system discloses a surgical stay and an annular frame. The annular frame conforms to the patient's body at the surgical site and has notches to receive and secure elastic members of surgical stays. The surgical stay also discloses a hook member in the elastic member forming a handle.

A surgical retractor system, such as that disclosed in U.S. Pat. No. 4,434,791 issued to W. Dale Darnell on Mar. 6, 1984, may comprise an array of standardized, interchangeable, annular retractor frame sections of various shapes of which the end portions are configured to permit the interchangeable, hinged connection of the various shaped frames. These frame sections generally are annular retractor units adaptable to conform to fit the surface contours of various patients upon which a surgical operation is to be performed. This retractor frame is designed to accept yielding rubber or like elastic stays. The retractor frame receives the elastic stays into notches which are integrally formed into the frame body. The elastic portion of the stay received by the retractor frame notch is in the form of a length of hollow elastic tubing adapted to be inserted into one of the notches of the frame and held in place by friction to retract the tissue. U.S. Pat. No. 5,769,783 issued to James M. Fowler on Jun. 23, 1998 discloses an example of a retractor frame having an annular flange with notches to receive the elastic member of a surgical retractor stay.

SUMMARY OF THE INVENTION

The present invention provides a sliding hook assembly for use with surgical retractor stay apparatus that offers several benefits over the prior art.

According to the present invention a surgeon may now employ a sliding hook assembly for securing a retractor stay apparatus in the absence of a surgical retractor stay frame. The sliding stay hook assembly of the present invention may be secured to a surgical drape or other physical restraint in or near the surgical field.

In one embodiment according to the invention the sliding hook assembly provides proximal and distal ends, the distal end of the sliding hook assembly encapsulating the distal portion of a hook member forming a handle body. The proximal portion of the sliding hook assembly includes an opening for receiving an elastic member and a tapered notch for securing the elastic member therein.

According to one embodiment of the present invention the hook member is of a configuration and the handle body is of a material that enables the handle body to hold the hook member without pull-out during use.

According to one embodiment of the present invention the hook member includes a wire-like portion that has at least one bend embedded within the handle body. The handle body is a molded member that closely conforms to the distal portion of the hook member. The handle body molded around the hook member may also function as a finger grip.

BRIEF DESCRIPTION OF THE DRAWINGS

FIG. 1 is a perspective view of the sliding hook assembly with a surgical retractor stay apparatus affixed therein;

FIG. 2 is a side sectional view of the surgical hook assembly showing the hook member encapsulated in the handle body;

FIG. 3 is a plan view of the sliding hook assembly showing the opening and notch in the proximal end of the sliding hook assembly and the hook member encapsulated in the handle body;

FIG. 4 is an end elevational view, as seen along lines 4—4 in FIG. 2, of the handle body and the hook portion extending therefrom;

FIG. 5 is a perspective view of the sliding hook assembly with a surgical retractor stay apparatus having a bifurcated hook member; and FIG. 6 is a perspective view of the sliding hook assembly with a surgical retractor stay apparatus having a multi-pronged hook member.

DETAILED DESCRIPTION OF INVENTION

One embodiment of the sliding hook assembly, as shown in FIG. 1, according to the present invention may be employed by a surgeon to secure a surgical retractor stay apparatus without requiring the use of a surgical retractor stay frame. The hook member of the sliding hook assembly may be secured to a surgical drape or other physical restraint in or near the surgical field. The hook member of the sliding hook assembly permits secure attachment of the sliding hook assembly to the physical restraint while also permitting the surgeon to detach the sliding hook assembly and to re-secure the sliding hook assembly at another point on the physical restraint. Alternatively, the hook member of the sliding hook assembly may be sized and shaped so as to permit the sliding hook assembly to be used with conventional surgical retractor frames such as disclosed in U.S. Pat. No. 5,785,649, which is fully incorporated herein by reference.

FIG. 1 shows one embodiment of the present invention, designated generally by the numeral 10, in which the elongated elastic member of a surgical retractor stay apparatus is received and secured. Sliding hook assembly 10 has a distal end 16 and a proximal end 18 as shown in FIGS. 1 and 3. The sliding hook apparatus 10 includes a hook member 12 that is partially embedded within the distal end 16 of the sliding hook assembly 10 forming a handle body 14 as shown in FIG. 2. A majority of the length of the hook member 12, i.e., the distal end 20 of the hook member 12, is embedded within the distal end 16 of the sliding hook assembly 10 to develop the connection between hook member 12 and handle body 14. This insures that the hook member 12 will not pull out of the handle body 14 during use. The handle body 14 of the sliding hook assembly 10 may also function as a finger grip surface allowing a surgeon to securely grasp sliding hook apparatus 10 when it is necessary or desirable to relocate the sliding hook apparatus 10 to a different attachment point on a physical restraint or to an alternate physical restraint in or near the surgical field.

In one embodiment according to the present invention the hook member 12, shown in FIGS. 2 and 3, is embedded within the handle body 14 by injection molding of a polymeric material to encapsulate the distal end 20 of the hook member 12 to form the handle body 14 of the sliding hook assembly 10. Thus, the sliding hook assembly 10 preferably has a one-piece injection molded structure of polymeric plastic material such as, for example, polyphenylene oxide (sold by General Electric under the trade name NORYL), polycarbonates and nylons encapsulating a portion of the hook member 12. This one-piece construction enables the sliding hook assembly 10 of the present invention to be autoclaved. Alternatively, the selection of inexpensive materials of construction for the sliding hook assembly permits the construction of a low-cost, disposable sliding hook assembly.

The details of construction of hook member 12 are shown in FIG. 2. The hook member 12 includes a large straight section 24 that communicates with a curved proximal end 22 of the hook member 12. The point 26 of hook member 12 may be sharp, rounded or blunt depending on the characteristics of the physical restraint that is engaged by the point 26. In one embodiment as shown in FIG. 2, the hook member 12 has a sharp point 26 for engaging a physical restraint such as a surgical drape. The proximal end 22 of the hook member 12 is generally semicircular, extending through an angle of about 180° as shown in FIG. 2. The curved proximal end 22 of the hook member 12 typically extends through an angle of from about 90° to about 180°. The proximal end 22 of the hook member 122 may also be sized and shaped so as to engage rectangular restraints.

The hook member 12 may include a wirelike portion having at least one bend embedded within the distal portion of the handle body. This permits configurations that are more resistant to pull-out of the hook member from the handle body. This resistance to pull-out may also be increased when the wirelike portion of the hook member 12 has at least two spaced apart bends that are embedded within the distal portion of the handle or when the embedded portion of the hook member 12 is an elongated member that is folded including multiple bends.

As shown in FIG. 2, bend 28 is provided for connecting straight section 30 with straight section 24. Bend 40 is provided for connecting straight section 30 with straight section 42. Curved arrow 32 in FIG. 2 shows the angular orientation between straight sections 24 and 30. In one embodiment according to the invention, the angle is approximately 45 degrees. Typically the angle represented by curved arrow 32 may range from about 90 degrees to about 180 degrees. Curved arrow 34 shows the angular orientation between straight sections 30 and 42. In one embodiment according to the present invention, the angle defined by curved arrow 34 is approximately 135 degrees. Typically the angle represented by curved arrow 34 may range from about 90 degrees to about 180 degrees. The angles selected for bend 28 and bend 40 are selected to fold the embedded portion of the hook member so as to improve resistance of the hook member to pull-out during use. Also the choice of the angles of bends 28 and 40 provide a method of shaping handle body 14 as a finger grip.

The proximal end 18 of the sliding hook assembly 10 includes an opening 36 for receiving an elastic member 50 as shown in FIGS. 1 and 3. The opening 36 in the proximal end 18 of the sliding hook assembly 10 is typically circular but may be any shape that permits the opening 36 to receive an elastic member. The opening 36 is typically located in the proximal end 18 of the sliding hook assembly 10 near the point at which the handle body 14 of the distal end 16 of the sliding hook assembly 10 transitions into the proximal end 18 of the sliding hook assembly 10.

As shown in FIG. 3, an indentation, channel or notch 38 extends from the opening 36. In one embodiment according to the present invention the notch 38 is approximately co-linear with the hook member 12, extending away from the hook member 12. However, the notch 38 may also be curvilinear or otherwise shaped so as to receive and secure an elastic member 50. Typically the notch 38, at the point of joining the opening 36, is approximately the width of an elastic member 50 to be inserted therein. The width of the notch 38 typically decreases as the notch 38 extends away from the opening 36. The decrease in width of the notch 38 permits increasing frictional forces to be applied to the elastic member 50 as the elastic member 50 is inserted further into the notch 38. The notch 38 permits an elastic member 50 to be frictionally secured therein while still permitting the surgeon to quickly and easily remove the elastic member 50 from the notch 38 in order to adjust or release the tension on the elastic member 50. Alternately, the surgeon may adjust or release the tension on the elastic member 50 by disengaging the hook member 12 of the sliding hook assembly 10 from the surgical drape or other physical restraint to which it is affixed.

In one embodiment according to the present invention the proximal end 18 and the distal end 16 of the sliding hook assembly 10 have approximately a perpendicular orientation with respect to one another as shown in FIGS. 1–4. The perpendicular orientation of the proximal end 16 and the distal end 18 of the sliding hook assembly improves stability of the sliding hook assembly 10 when the hook member 12 is engaged in a physical restraint and the proximal end 18 of the sliding hook assembly 10 rests on a support surface.

FIGS. 1, 5 and 6 show three embodiments according to the present invention of a sliding hook assembly system having a sliding hook assembly 10 and a surgical retractor stay apparatus. The sliding hook assembly system as shown in FIG. 1 includes the sliding hook assembly 10 as previously described and further includes the surgical retractor stay apparatus 44. The surgical stay retractor apparatus 44 comprises an elongated elastic member 50 having a distal end 49 and a proximal end 51, a hook member 56 having a distal end (not shown) and a proximal end 62 and a restriction band 52. The distal end of the hook member 56 is received by the distal end 49 of the elastic member 50. The restriction band 52 encompasses the distal end 49 of the elastic member 50 which received the distal end of the hook member 56. The restriction band 52 further encompasses a portion of the hook member 56 extending beyond the elastic member 50 and encompasses a small portion of the elastic member 50 beyond the point at which the hook member 56 is received. The restriction band 52 may be made of, for example, resilient elastic materials or shrink wrap materials. The hook member 56 has a curved portion 65 which typically extends through a bend of 180° and typically ends in a sharp point 64. The curved portion 65 of hook member 56 typically extends through a bend of from about 90 degrees to about 180 degrees.

FIG. 5 shows a second embodiment according to the present invention of the sliding hook assembly system comprising the sliding hook assembly 10 and a surgical retractor stay apparatus 46. The retractor stay apparatus 46 has an elongated elastic member 50 having a distal end 49 and a proximal end 51, a bifurcated hook member 58 having a distal end (not shown) and a proximal end 59 and a restriction band 52. The distal end 49 of the elastic member 50 receives the distal end of the hook member 58. The restriction band 52 encompasses that portion of the elastic member 50 receiving the distal end of the hook member 58 to prevent the hook member 58 from pulling out of elastic member 50 during use. The restriction band 52 extends to cover a portion of the hook member 58 external to the elastic member 50 and also extends over a portion of the distal end 49 of the elastic member 50 beyond the point at which the distal end of the hook member 58 is received. The hook member 58 is bifurcated having two arms 66a and 66b, each of which has a curved portion 67a and 67b typically ending in a sharp point 68a and 68b. The curved portions 67a and 67b typically bend through a range of from about 120 degrees to about 180 degrees. In one embodiment according to the present invention the curved portions 68a and 68b extend through a bend of approximately 180 degrees.

FIGS. 6 shows a third embodiment according to the present invention having a sliding hook assembly 10 and a surgical retractor stay apparatus 48. The surgical stay apparatus 48 comprises an elongated elastic member 50 having a distal end 49 and a proximal end 51, a paddle member 70 having a distal end 69 and a proximal end 71, and a restriction band 52. The paddle member 70 includes a handle 73 a portion of which is received by the distal end of the elastic member 50. The restriction band 52 encompasses the distal end 49 of the elastic member 50 that has received the handle 73 of the paddle member 70. The restriction band 52 extends in both directions beyond that portion of the elastic member 50 that has received a portion 60 of the paddle member 70. The restriction band 52 reduces the possibility of pull-out of the paddle member 70 from the elastic member 50 during use in a surgical procedure. The proximal end 71 of the paddle member 70 has a plurality of prongs 72 which typically extend through a bend of from about 120 degrees to about 180 degrees.

One method according to the present invention includes the steps of securing the hook member 12 of the sliding hook assembly 10 to a physical restraint, for example a surgical drape; securing the elastic member 50 of a surgical retractor stay in the notch 38; engaging tissue with the tissue holding member; and removing the sliding hook assembly 10 and stay after completing the surgical procedure.

Another method according to the present invention includes the steps of placing a surgical retractor frame around a surgical site; securing the hook member 12 of the sliding hook assembly 10 to the surgical retractor frame; securing the elastic member 50 of a surgical retractor stay in the notch 38; engaging tissue with the tissue holding member; and removing the sliding hook assembly 10, surgical retractor frame and stay after completing the surgical procedure.

Thus, the sliding hook assembly according to the present invention provides a sliding hook assembly for securing a retractor stay apparatus without requiring, but permitting, the use of a surgical retractor frame. The sliding hook assembly may be secured to a surgical drape or other physical restraint in or near the surgical field. The hook member of the sliding hook assembly permits secure attachment of the sliding hook assembly while also permitting the surgeon to easily and quickly move the sliding hook assembly to another point on the physical restraint.

The foregoing disclosure and description of the invention are illustrative and explanatory thereof, and various changes in the details of the illustrated apparatus and construction and method of operation may be made without departing from the spirit of the invention.

I claim:

1. A sliding hook assembly for use with a surgical stay elastic member comprising:

(a) a handle body having proximal and distal end portions;
    (b) a hook member having proximal and distal end portions, a portion of the hook member being encapsulated by the handle body;
    (c) an opening in the proximal end of the handle body for receiving an elastic member; and
    (d) the opening communicating with a notch for securing the elastic member.

2. The sliding hook assembly of claim 1, wherein the handle body is a molded member that closely conforms to the distal portion of the hook member.

3. The sliding hook assembly of claim 1, wherein a majority of the distal portion of the hook member is encapsulated by the distal portion of the handle body.

4. The sliding hook assembly of claim 1, wherein the hook member has an exposed curved portion extending from the distal portion of the handle body.

5. The sliding hook assembly of claim 1, wherein the hook member includes a wirelike portion that has at least one bend embedded within the distal portion of the handle body.

6. The sliding hook assembly of claim 1, wherein the hook member includes a wirelike portion that has at least two spaced apart bends that are embedded within the distal portion of the handle body.

7. The sliding hook assembly of claim 1, wherein the exposed portion of the hook member extends through a bend of about 120 degrees to about 180 degrees.

8. The sliding hook assembly of claim 1, wherein the handle body contains an embedded distal portion of the hook member that is much longer than the exposed hook portion.

9. The sliding hook assembly of claim 1, wherein the embedded distal portion of the hook member is an elongated member that is folded including multiple bends.

10. The sliding hook assembly of claim 1, wherein the notch is tapered to a width less than the width of the elastic member.

11. The sliding hook assembly of claim 1, wherein the proximal and distal end portions of the handle body are approximately perpendicular to one another.

12. The sliding hook assembly of claim 1, wherein the handle body comprises a polymeric plastic material.

13. The sliding hook assembly of claim 12, wherein the polymeric material is selected from the group consisting of polyphenylene oxide, polycarbonates and nylons.

14. A sliding hook assembly system comprising:
   (a) a surgical retractor stay apparatus having an elastic member having a width and a stay hook member received by the elastic member; and
   (b) a sliding hook assembly comprising:
      (1) a handle body having proximal and distal end portions;
      (2) a hook member having proximal and distal end portions, a portion of the hook member being encapsulated by the handle body;
      (3) an opening in the proximal end of the handle body for receiving the elastic member; and
      (4) the opening communicating with a notch for securing the elastic member.

15. The sliding hook assembly system of claim 14 wherein the surgical retractor stay apparatus further comprises a restriction band encapsulating the distal end of the elastic member.

16. The sliding hook assembly system of claim 14, wherein the handle body is a molded member that closely conforms to the distal portion of the hook member.

17. The sliding hook assembly system of claim 14, wherein a majority of the distal portion of the hook member is encapsulated by the distal portion of the handle body.

18. The sliding hook assembly system of claim 14, wherein the hook member has an exposed curved portion extending from the distal portion of the handle body.

19. The sliding hook assembly system of claim 14, wherein the hook member includes a wirelike portion that has at least one bend embedded within the distal portion of the handle body.

20. The sliding hook assembly system of claim 14, wherein the hook member includes a wirelike portion that has at least two spaced apart bends that are embedded within the distal portion of the handle body.

21. The sliding hook assembly system of claim 14, wherein the exposed portion of the hook member extends through a bend of about 120 degrees to about 180 degrees.

22. The sliding hook assembly system of claim 14, wherein the embedded distal portion of the hook member is an elongated member that is folded including multiple bends.

23. The sliding hook assembly system of claim 14, wherein the notch is tapered to a width less than the width of the elastic member.

24. The sliding hook assembly system of claim 14, wherein the proximal and distal end portions of the handle are approximately perpendicular to one another.

25. The sliding hook assembly system of claim 14 wherein a portion of the stay hook member extends through a bend of from about 90 degrees to about 180 degrees.

26. The sliding hook assembly system of claim 25 wherein said curved portion of the stay hook member has a bifurcated portion including two arms each having a point.

27. The sliding hook assembly system of claim 25 wherein the stay hook member comprises a paddle having a plurality of prongs.

28. A sliding hook assembly system comprising:
   (a) a frame that conforms to a patient's body at a surgical site;
   (b) a surgical retractor stay apparatus having an elastic member and a stay hook member received by the elastic member; and
   (c) a sliding hook assembly comprising:
      (1) a handle body having proximal and distal end portions;
      (2) a hook member having proximal and distal end portions, a portion of the hook member being encapsulated by the handle body;
      (3) an opening in the proximal end of the handle body for receiving an elastic member; and
      (4) the opening communicating with a notch for securing the elastic member.

29. The sliding hook assembly system of claim 28 wherein the surgical retractor stay apparatus further comprises a restriction band encapsulating the distal end of the elastic member.

30. The sliding hook assembly system of claim 28, wherein the handle body is a molded member that closely conforms to the distal portion of the hook member.

31. The sliding hook assembly system of claim 28, wherein a majority of the distal portion of the hook member is encapsulated by the distal portion of the handle body.

32. The sliding hook assembly system of claim 28, wherein the hook member has an exposed curved portion extending from the distal portion of the handle body.

33. The sliding hook assembly system of claim 28, wherein the hook member includes a wirelike portion that has at least one bend embedded within the distal portion of the handle body.

34. The sliding hook assembly system of claim 28, wherein the hook member includes a wirelike portion that has at least two spaced apart bends that are embedded within the distal portion of the handle body.

35. The sliding hook assembly system of claim 28, wherein the exposed portion of the hook member extends through a bend of about 120 degrees to about 180 degrees.

36. The sliding hook assembly system of claim 28, wherein the embedded distal portion of the hook member is an elongated member that is folded including multiple bends.

37. The sliding hook assembly system of claim 28, wherein the notch is tapered to a width less than the width of the elastic member.

38. The sliding hook assembly system of claim 28, wherein the proximal and distal end portions of the handle are approximately perpendicular to one another.

39. The sliding hook assembly system of claim 28, wherein a portion of the stay hook member extends through a bend of from about 90 degrees to about 180 degrees.

40. The sliding hook assembly system of claim 28, wherein the stay hook member has an exposed bifurcated portion including two arms each having a point and wherein the two arms each extend through a bend of from about 120 degrees to about 180 degrees.

41. The sliding hook assembly system of claim 28 wherein the hook member comprises a paddle having a plurality of prongs and the prongs each extending through a bend of from about 120 degrees to about 180 degrees.

42. A method of retracting tissue at an incision during surgery upon a portion of a patient's body at a surgical site, comprising the steps of:
   (a) securing a sliding hook assembly to a restraint, the sliding hook assembly comprising:
      (1) a handle body having proximal and distal end portions;
      (2) a hook member having proximal and distal end portions, a portion of the hook member being encapsulated by the handle body;

(3) an opening in the proximal end of the handle body for receiving the elastic member; and (4) the opening communicating with a notch for securing the elastic member;

(b) attaching a surgical retractor stay having an elongated elastic member and a tissue holding member by securing the elastic member in the notch of the sliding hook assembly and engaging tissue with the tissue holding member; and (c) removing the sliding hook assembly and stay after completing the surgical procedure.

43. The sliding hook assembly system of claim 42, wherein the handle body is a molded member that closely conforms to the distal portion of the hook member.

44. The sliding hook assembly system of claim 42, wherein the hook member includes a wirelike portion that has at least two spaced apart bends that are embedded within the distal portion of the handle body.

45. The sliding hook assembly system of claim 42, wherein the embedded distal portion of the hook member is an elongated member that is folded including multiple bends.

46. The sliding hook assembly system of claim 42, wherein the notch is tapered to a width less than the width of the elastic member.

47. The sliding hook assembly system of claim 42, wherein the proximal and distal end portions of the handle are approximately perpendicular to one another.

48. A method of retracting tissue at an incision during surgery upon a portion of a patient's body at a surgical site, comprising the steps of:

(a) fitting a frame to a patient's body at a surgical site;

(b) securing a sliding hook assembly to the frame, the sliding hook assembly comprising:

(1) a handle body having proximal and distal end portions;

(2) a hook member having proximal and distal end portions, a portion of the hook member being encapsulated by the handle body;

(3) an opening in the proximal end of the handle body for receiving the elastic member; and (4) the opening communicating with a notch for securing the elastic member;

(c) attaching a surgical retractor stay having an elongated elastic member and a tissue holding member by securing the elastic member in the notch of the sliding hook assembly and engaging tissue with the tissue holding member; and (d) removing the sliding hook assembly, frame and stay after completing the surgical procedure.

49. The sliding hook assembly system of claim 48, wherein the handle body is a molded member that closely conforms to the distal portion of the hook member.

50. The sliding hook assembly system of claim 48, wherein the hook member includes a wirelike portion that has at least two spaced apart bends that are embedded within the distal portion of the handle body.

51. The sliding hook assembly system of claim 48, wherein the embedded distal portion of the hook member is an elongated member that is folded including multiple bends.

52. The sliding hook assembly system of claim 48, wherein the notch is tapered to a width less than the width of the elastic member.

53. The sliding hook assembly system of claim 48, wherein the proximal and distal end portions of the handle are approximately perpendicular to one another.

* * * * *

UNITED STATES PATENT AND TRADEMARK OFFICE
CERTIFICATE OF CORRECTION

PATENT NO. : 5,964,698
DATED : October 12, 1999
INVENTOR(S) : James M. Fowler

It is certified that error appears in the above-identified patent and that said Letters Patent is hereby corrected as shown below:

In column 5, line 44, delete "68a and 68b" and insert --67a and 67b--.

In column 6, claim 7, line 56, delete "wherein the" and insert --wherein an--.

In column 6, claim 8, line 60, delete "embedded" and insert --encapsulated--.

In column 6, claim 8, line 61, delete "the" and insert --an--.

In column 6, claim 9, line 63, delete "embedded" and insert --encapsulated--.

In column 7, claim 15, line 24, delete "the distal" and insert --a distal--.

In column 7, claim 21, line 44, delete "wherein the" and insert --wherein an--.

In column 7, claim 22, line 47, delete "embedded" and insert --encapsulated--.

In column 7, claim 26, line 60, delete "said curved" and insert --the--.

In column 8, claim 29, line 16, delete "the distal" and insert --a distal--.

In column 8, claim 35, line 36, delete "wherein the" and insert --wherein an--.

UNITED STATES PATENT AND TRADEMARK OFFICE
CERTIFICATE OF CORRECTION

PATENT NO. : 5,964,698
DATED : October 12, 1999
INVENTOR(S) : James M. Fowler

It is certified that error appears in the above-identified patent and that said Letters Patent is hereby corrected as shown below:

In column 8, claim 36, line 39, delete "wherein the" and insert --wherein an--.

In column 9, claim 45, line 20, delete "wherein the" and insert --wherein an--.

In column 10, claim 51, line 25, delete "wherein the" and insert --wherein an--.

Signed and Sealed this

First Day of August, 2000

Q. TODD DICKINSON

*Attest:*

*Attesting Officer*     *Director of Patents and Trademarks*